(12) United States Patent
Glickman

(10) Patent No.: US 8,038,644 B2
(45) Date of Patent: Oct. 18, 2011

(54) CATHETER

(75) Inventor: Scott Glickman, Buckinghamshire (GB)

(73) Assignee: Jotillou Enterprises Ltd. (GB)

( * ) Notice: Subject to any disclaimer, the term of this patent is extended or adjusted under 35 U.S.C. 154(b) by 0 days.

(21) Appl. No.: 12/597,888

(22) PCT Filed: Apr. 10, 2008

(86) PCT No.: PCT/GB2008/001253
§ 371 (c)(1),
(2), (4) Date: Apr. 12, 2010

(87) PCT Pub. No.: WO2008/132431
PCT Pub. Date: Nov. 6, 2008

(65) Prior Publication Data
US 2010/0198139 A1    Aug. 5, 2010

(30) Foreign Application Priority Data
May 1, 2007  (GB) .................................. 0708427.0

(51) Int. Cl.
*A61M 1/00* (2006.01)
*A61M 3/00* (2006.01)
*A61M 37/00* (2006.01)
*A61M 29/00* (2006.01)

(52) U.S. Cl. ....... 604/30; 604/43; 604/96.01; 604/99.01
(58) Field of Classification Search .................. 604/246, 604/96.01, 30, 43, 97.01–97.02, 99.01–99.03, 604/103.03, 101.01
See application file for complete search history.

(56) References Cited

U.S. PATENT DOCUMENTS

| 3,331,371 A | 7/1967 | Rocchi et al. |
| 3,394,705 A | 7/1968 | Abramson |
| 3,981,299 A | 9/1976 | Murray |
| 4,150,673 A * | 4/1979 | Watt .............................. 604/408 |

(Continued)

FOREIGN PATENT DOCUMENTS

GB    1534219 A    11/1978

(Continued)

OTHER PUBLICATIONS

"Great Britain Application Serial No. GB0708427.0, United Kingdom Search Report mailed Jul. 25, 2007", 3 pgs.

(Continued)

*Primary Examiner* — Theodore Stigell
*Assistant Examiner* — Bradley Thomas, Jr.
(74) *Attorney, Agent, or Firm* — Schwegman, Lundberg & Woessner, P.A.

(57) ABSTRACT

A catheter (200) for insertion into a hollow viscus of a subject, comprising: a drainage opening (204) and an instillation opening at a distal end an inlet port (209) at a proximal end for instilling a fluid; an outlet port (205) at the proximal end for draining fluid from the viscus; a drainage channel (201) connecting the drainage opening to the outlet port; an instillation channel (211) connecting the inlet port to the instillation opening; a valve (223) proximate the drainage channel at the distal end for closing it against the entry of fluid from the viscus; a valve control port (220) at the proximal end for receiving a control fluid under pressure; and a control channel (222) connecting the valve control port to the valve such that the valve is responsive to admitted control fluid under pressure to close itself.

18 Claims, 2 Drawing Sheets

U.S. PATENT DOCUMENTS

Figure 1:
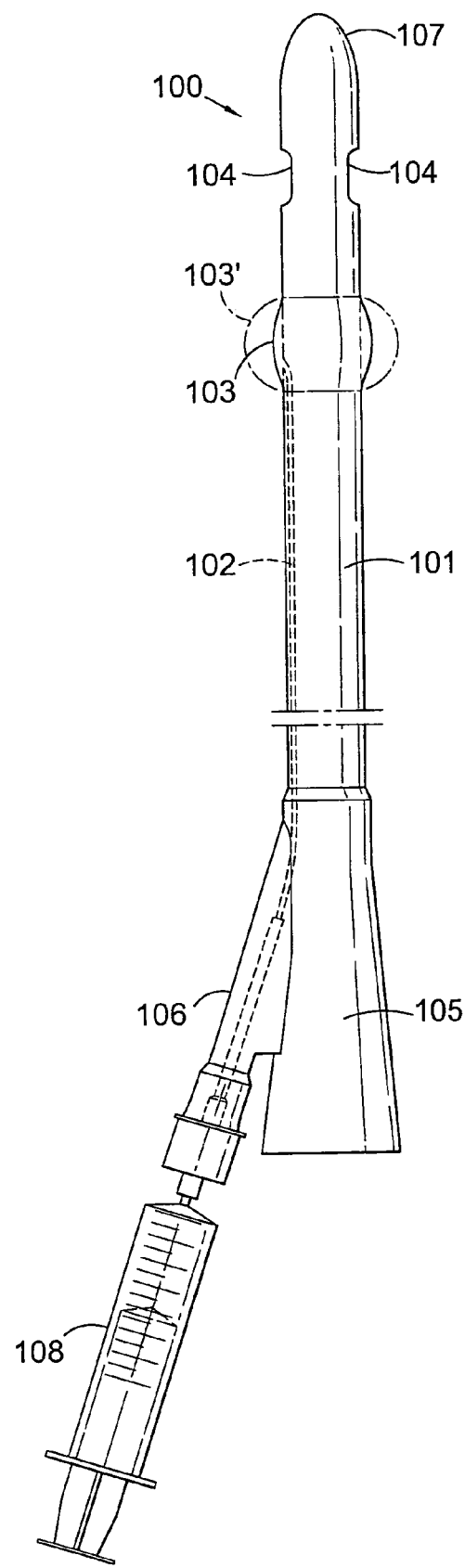

| | | | |
|---|---|---|---|
| 4,227,533 A | 10/1980 | Godfrey | |
| 5,085,636 A | 2/1992 | Burns | |
| 5,112,306 A * | 5/1992 | Burton et al. | 604/101.02 |
| 5,792,118 A * | 8/1998 | Kurth et al. | 604/246 |
| 5,971,972 A | 10/1999 | Rosenbaum | |
| 6,093,191 A | 7/2000 | Porter | |
| 2006/0173419 A1* | 8/2006 | Malcolm | 604/246 |
| 2006/0195059 A1* | 8/2006 | Freyman et al. | 604/96.01 |

FOREIGN PATENT DOCUMENTS

| | | |
|---|---|---|
| WO | WO-02/28465 A1 | 4/2002 |

OTHER PUBLICATIONS

"International Application Serial No. PCT/GB2008/001253, International Search Report mailed Jul. 14, 2008", 5 pgs.

"European Application Serial No. 08736924.5, Office Action dated Nov. 24, 2010", 3 pgs.

"European Application Serial No. 08736924.5, Response filed Dec. 14, 2010 to Office Action dated Nov. 24, 2010", 13 pgs.

"Great Britain Application Serial No. GB0708427.0, Examination Report dated Mar. 16, 2009", 1 pg.

"Great Britain Application Serial No. GB0708427.0, Response filed Sep. 2, 2008 to Search Report mailed Jul. 25, 2007", 5 pgs.

"International Application Serial No. PCT/GB2008/001253, International Preliminary Examination Report dated Nov. 3, 2009", 4 pgs.

"Russian Application No. 2009144279, Office Action dated Feb. 8, 2010", 3 pgs.

"Russian Application No. 2009144279, Response filed Apr. 2, 2010 to Office Action dated Feb. 8, 2010", 4 pgs.

* cited by examiner

CATHETER

Related Applications

This application is a nationalization under 35 U.S.C. 371 of PCT/GB2008/001253, filed Apr. 10, 2008 and published as WO 2008/132431 A1 on Nov. 6, 2008, which claimed priority under U.S.C. 119 to United Kingdom Application No. 0708427.0, filed May 1, 2007, which applications and publication are incorporated herein by reference and made a part hereof.

This invention relates to a catheter for draining a hollow viscus such as the urinary bladder of a human or animal subject.

Overactive bladders currently are treated with oral antimuscarinic agents that act as competitive antagonists to acetylcholine, secreted from excitatory nerves that act on bladder muscle (detrusor) receptors. The antimuscarinic agents taken as oral medications also act on many receptors in other tissues in the body. When they do so the effects are known as side effects. If the side effects are dangerous or contribute to morbidity they are known as adverse side effects or adverse reactions. Oral antimuscarinic agents used to suppress bladder activity commonly produce side effects and can produce adverse side effects. Atropine sulphate, instilled into the urinary bladder, has been shown to be efficacious, through physiological and clinical trials as a suppressor of detrusor activity and has been statistically demonstrated to have a more favourable side effect profile than oral medication. However, a reliable and easy-to-use delivery system needs to be available in order for this treatment to be utilised by the people who could benefit from this application of this drug.

Urinary tract infections (UTI) are considered to be the commonest hospital acquired infections and probably constitute 30-40% of all infections acquired in such healthcare settings. They commonly result from catheterisation of urinary bladders. Treatment of people with urinary tract infections typically is by means of antibiotics delivered as oral or parenteral agents. The drugs are absorbed into the "system," excreted by the kidneys into urine and delivered to the site of action in the bladder. In both cases drug efficacy is subject to physical characteristics of the drug preparations such as tablet or capsule disintegration rates and subsequent dissolution in the aqueous mediums of the alimentary tract. Furthermore other substances that form complexes with drug molecules may interfere with their efficient passage across the intestinal wall. Furthermore, there are individuals' physiological characteristics that affect the pharmacokinetics of the drugs i.e. variables that influence delivery of active drugs unchanged by metabolism and/or as active metabolites. This is known as drug bioavailability. Unfortunately, many antibiotic agents active against urinary tract organisms delivered orally or parenterally can produce unpleasant and adverse side effects including allergic reactions.

The urinary bladder being a common source of community and hospital acquired morbidity through infections is an issue of great importance in clinical medicine. Indeed, infections of the urinary bladder can progress to septicaemia and thus pose mortal risks. An important principle of therapeutics is that drug treatments should be delivered by the most logical route to maximise on safety and efficacy with minimal associated side effects. For treatments that require repeated drug administration such as antibiotic courses or for long-term treatments of chronic conditions such as overactive bladders it also is important to consider treatment acceptability in selecting the route of administration. To date the opportunities for intravesical treatments have been limited, because current methods of accessing the urinary bladder, and particularly for self-administration of drugs, require substantial manual dexterity and are time-consuming and therefore would generally not be tolerated by patients for repetitive use.

Current treatment of urinary bladder cancers includes instillations of cytotoxic chemotherapy agents. This procedure typically is performed in hospital and requires the patient to roll around on the bed or plinth after the drug is instilled to enable the drug to become coated over the entire mucosal lining of the bladder. The procedure commonly is tiring and unpleasant. After treatment the patient typically is advised to rest in hospital and then to return home to rest. It would be much more tolerable if the drug could be administered in the domiciliary setting, so that the patient can fall asleep or rest immediately in the comfort of his/her own home.

The purpose of the present invention is to overcome the limitations of existing instruments for treatment of such conditions.

The present invention provides a catheter for insertion into a hollow viscus of a subject, comprising: a drainage opening and an instillation opening at a distal end; an inlet port at a proximal end for instilling a fluid; an outlet port at the proximal end for draining fluid from the viscus; a drainage channel connecting the drainage opening to the outlet port; an instillation channel connecting the inlet port to the instillation opening; a valve proximate the drainage channel at the distal end for closing it against the entry of fluid from the viscus; a valve control port at the proximal end for receiving a control fluid under pressure; and a control channel connecting the valve control port to the valve such that the valve is responsive to admitted control fluid under pressure to close itself.

The catheter according to the invention enables an effective, reliable and relatively easy installation of drugs to the hollow viscus such as the urinary bladder. The valve for closing the drainage channel prevents loss of the drug (or other instillation fluid) and also prevents unwanted drainage of urine from the viscus following drug installation.

Accordingly, the invention provides for a safer, more reliable and, for some patients more acceptable method of obtaining active antibiotic treatment for the urinary bladder, by using direct intravesical instillations. This delivery system is acceptable for repetitive treatment as is necessary for antibiotic efficacy; and the system can be manufactured relatively inexpensively.

Prophylaxis and active treatment via intravesical administration of antibiotics or other drugs following catheterisation enables precisely the desired quantity of active drug to be delivered to the site of action immediately. However, as treatment of urinary tract infections may require exposure of the antibiotics to the bacteria within the bladder for several days and as detrusor suppression for neurogenic bladder overactivity with intravesical antimuscarinic agents, such as atropine sulphate, is best maintained continuously, it is necessary to ensure that drugs can be continuously available. As the unabsorbed drugs in the bladder are washed out with micturition i.e. urine drainage by urination or drainage by other means from the bladder, the drugs would need to be replenished at the site of action in the cavity of the urinary bladder. This invention enables repetitive drug instillations into the urinary bladder using intermittent catheterisation, which is well established in clinical healthcare, is generally tolerated well by patients and can be used by them independently of healthcare professionals.

The invention enables treatment of urinary bladder cancers to be undertaken by the patient in his or her own home. It provides an intravesical drug delivery system that is reliable, tolerably easy to use, and relatively inexpensive. This domiciliary procedure could be delivered by a qualified healthcare professional such as a district nurse or specialist urology or continence nurse, saving on the resources of hospitals significantly. This treatment approach is consistent with the current philosophy that, with regard to the quality of life for patients, and when it is considered safe to do so, treatments are best delivered in patients' homes.

Figure 2:
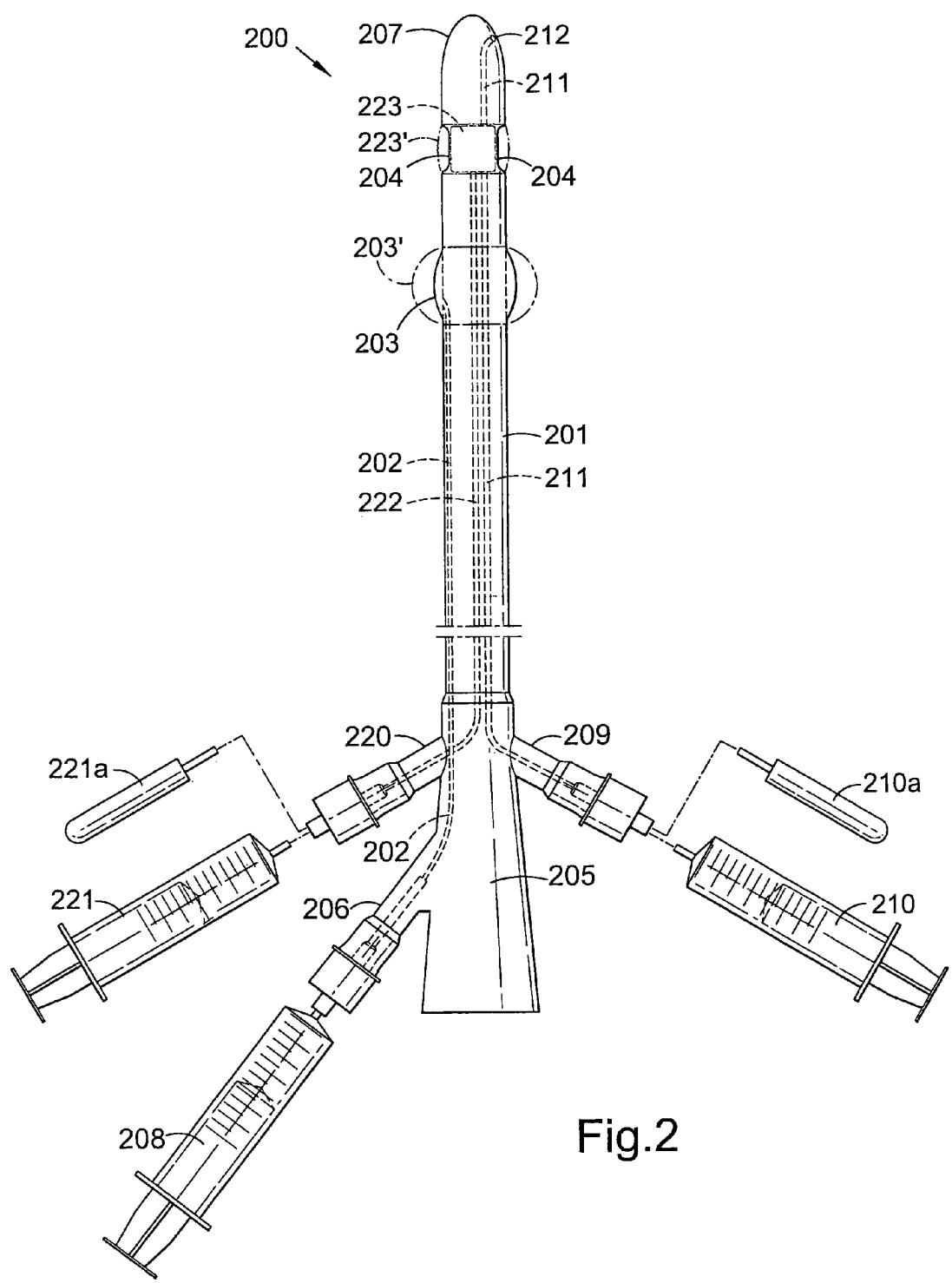

In order that the invention may be better understood, a preferred embodiment will now be described with reference to the accompanying drawings, in which:

FIG. 1 is a diagrammatic view of a conventional catheter with a balloon inflation channel; and FIG. 2 is a corresponding view of a catheter embodying the present invention.

A Foley catheter is illustrated in FIG. 1. The catheter 100 has a closed tip 107 at its distal end and a drainage port 105 at its proximal end connected through a drainage channel 101 to a pair of openings 104 in the catheter wall, at the distal end. Foley catheters are flexible, usually of Latex (trade mark) or a silicone-based plastics material, and are passed through the urethra during urinary catheterisation and into the bladder to drain urine. A balloon 103 close to the distal end is connected through a balloon control channel 102 within the catheter to a balloon control port 106 at the proximal end. The balloon 103 is inflatable to a position 103' by the injection of sterile water, for example from a syringe 108, into the port 106. The water causes the balloon 103 to inflate so as to increase substantially the diameter of the catheter close to its distal end, in order to retain or anchor the catheter within the bladder. Withdrawal of the catheter is effected by first deflating the balloon and then withdrawing it through the urethra.

Intermittent catheters designed for bladder drainage of urine reportedly reduce the incidence of catheter-acquired urinary tract infections. For ease of insertion through the urethra, they are typically coated with a chemical that becomes very slippery when water is applied to it. The chemical is referred to as "hydrophilic," because it combines with water molecules. Thus the hydrophilic coating enables the catheter to be inserted through the urethra with a very low friction producing no friction trauma damage to the urethral mucosa. For repetitive catheterisations patients appear to prefer to be catheterised with intermittent catheters.

Foley balloons, a feature of most indwelling catheters, are provided typically in two different sizes: 5 cc and 30 cc. The relative size of a Foley catheter is described using French units, F: 1 F is equivalent to 0.33 mm of diameter. Thus the size in French units is roughly equal to the circumference of the catheter in millimetres. Foley catheters typically range from 10 F to 28 F.

Foley catheters are available in several sub-types. Coudé (meaning "elbowed") catheters have a 45 degree bend at the tip to allow easier access through an enlarged prostate. Council tip catheters have a small hole at the tip which allows them to be passed over a wire. Three way catheters are used primarily after bladder or prostate cancer or prostate surgery. They have a third arm or bell (not shown) that allows an irrigant to pass to the tip of the catheter through a small separate channel into the bladder. This serves to wash away blood and small clots through the primary arm that drains into a collection device connected to the port 105. This prevents larger clots that might plug the catheter from forming. The second or inflation arm (corresponding to port 106) has a small plastic valve that allows for the introduction or removal of sterile water through a very small channel to inflate or deflate the retaining balloon.

A catheter embodying the present invention is shown in FIG. 2. This has several parts in common with the Foley catheter of FIG. 1, including the tip 207, the pair of inlet ports 204 at the proximal end communicating with the drainage channel 201 and the outlet port 205. The Foley balloon 203, 203' is connected to a balloon control channel 202 and thus to a balloon control port 206 which may be arranged to receive sterile water under pressure from a syringe 208, as is well known. Preferably, the catheter is coated with a hydrophilic layer, to make it very slippery, allowing its use as an intermittent catheter.

In an alternative embodiment of the invention (not shown), the catheter is not of the Foley type and accordingly does not have the balloon 203. Some other means may be provided to retain the catheter in its operative position.

A separate intraluminal channel 211 connects an inlet port 209 to an instillation opening 212 at the distal end of the catheter and preferably near the tip of the catheter, for the instillation of a fluid such as a pharmaceutical preparation. This instillation channel 211 is a canalicula incorporated into the wall of the catheter as an independent channel. Delivery of the fluid, such as a drug with a suitable delivery agent, is from a suitable syringe 210, or else a storage reservoir 210a which may be incorporated as part of the catheter device. For example, the reservoir may be in the form of a plastics capsule with a breakable seal, such that pressure applied to its walls break the seal and squeeze the contents into the port 209. The storage reservoir or capsule arrangement is advantageous because it allows the drug and the delivery system effectively to be provided as an integral unit such that fluids may be delivered through the instillation channel into the hollow viscus. With the syringe attachment option, multiple instillations may be delivered sequentially by attachment and detachment of instillation devices such as syringes. Typically, the canalicula 211 contains less than 1 ml of the fluid, so very little is wasted.

The catheter 200 may be of the same diameter and length as the catheters currently available such as Foley catheters described above. However, they may be provided at greater lengths, to facilitate easier handling during self-administration of instillation fluids. Thus the length of the catheter could be in the range of for example 30 cm to 1 m.

A plastics balloon 223, similar in type to a Foley balloon, is disposed within the walls of the catheter and is inflatable to a position 223' through a control channel 222 by means of a viscous fluid such as a gel, supplied under pressure from a valve control port 220 to which the control channel is connected. An expandable foam or other suitable substance could be used instead of a gel as the control fluid, to distend the valve balloon. The balloon 223 constitutes a valve for closing the drainage channel 201. In this example, the balloon valve 223 is adjacent the inlet ports 204 which are elongate apertures in the wall of the catheter. Since the balloon has flexible walls, once it is inflated under the fluid pressure it expands to engage fully against the edges of the inlet openings 204 to provide a fluid tight seal. This prevents urine from the bladder being drained.

The control channel 222 is a canalicula, i.e. a very narrow bore channel. The viscous gel is supplied under pressure from a syringe 221 or else from a plastics capsule 221a which may be formed integrally with the catheter. The capsule 221a may have a breakable seal, although this is not considered necessary. Application of pressure by the user to the walls of the capsule 221a forces the gel into the balloon 223 to inflate it fully. Due to the viscosity of the gel and the narrow bore of the control channel 222, fluid flow is effectively one way, since there is insufficient pressure from the balloon to force the gel back towards the port 220. Accordingly, the balloon stays inflated even when pressure on the capsule 221a, or alternatively the syringe 221, is reduced or eliminated. Since this form of catheter is intended to be used only once, this is desirable.

Thus closure of the valve, constituted by the balloon 223, prevents any further back-flow drainage of urine, instillation fluid or other fluid in the hollow viscus through the lumen of the catheter and thus out of the body, and it does so without allowing the catheter channel 201 to provide any trapping of the instilled fluid within the lumen. Thus the integrity of flow through the instillation channel is not compromised by pressure exerted from the intraluminal inflation balloon even in its fully inflated state.

Since no instillation fluid is lost through drainage from the hollow viscus, the medical practitioner using the catheter is able to know the precise volume of drug or other fluid that has been instilled into the hollow viscus.

The types of drug that are suitable for use with the catheter will of course be well known to the medical practitioners and would depend upon the condition being treated. They could include antimuscarinic agents, antibiotics, cytotoxic agents, corticosteriods and local anaesthetics.

In order to avoid errors in its use, the ports 220, 206 and 209 i.e. the arms at the proximal end of the catheter are preferably colour coded to distinguish them from one another. Preferably also they are configured with different shapes or sizes to avoid errors.

By way of example, overactive bladders may be treated effectively with Atropine Sulphate, and this drug may be supplied integrally, in a capsule 210a, with the catheter 200.

The method of use of the catheter 200 for instilling a drug into a human bladder will now be described. First, the catheter is inserted either through the urethra or through a surgically created opening in the bladder wall. If the catheter has a Foley balloon, then this can be inflated to anchor the catheter in place. Once the urine has drained, the valve is closed, blocking the end of the drainage channel 201 and preventing further drainage of fluid from the bladder. The drug is then instilled into the bladder, and the catheter is then removed from the bladder, including deflating the Foley balloon if necessary. The catheter system is then discarded.

The invention claimed is:

1. A catheter for insertion into a hollow viscus of a subject, comprising:
   a drainage opening and an instillation opening at a distal end;
   an inlet port at a proximal end for instilling an instillation fluid;
   an outlet port at the proximal end for draining fluid from the viscus;
   a drainage channel connecting the drainage opening to the outlet port;
   an instillation channel connecting the inlet port to the instillation opening;
   a valve that is located proximate the drainage opening at the distal end for closing the drainage channel against the entry of fluid from the viscus;
   a valve control port at the proximal end for receiving a control fluid under pressure;
   and a control channel connecting the valve control port to the valve such that the valve is responsive to admitted control fluid under pressure to close the drainage channel, the catheter being such that flow of the control fluid to the valve is one way and the valve stays closed after the control fluid has entered the catheter under pressure.

2. A catheter according to claim 1, in which the valve comprises a balloon inflated by the control fluid to obstruct the drainage channel.

3. A catheter according to claim 1, comprising a reservoir of the control fluid connected to the valve control port for selective actuation by a user.

4. A catheter according to claim 1, comprising a balloon adjacent an external wall of the catheter near its distal end and connected through a balloon control channel to a balloon control port at the proximal end, the balloon being inflatable and deflatable to respectively increase and decrease the local diameter of the catheter to allow temporary anchoring of the catheter within the hollow viscus.

5. A catheter according to claim 1, in which the external wall of the catheter is coated with a hydrophilic layer.

6. A catheter according to claim 1, in which the ports at the proximal end are colour coded to distinguish them from one another.

7. A catheter according to claim 1, in which the ports at the proximal end are distinguishable from one another by having different shapes.

8. A catheter according to claim 1, comprising a reservoir of a fluid pharmaceutical preparation connected to the instillation opening.

9. A catheter according to claim 8, in which the fluid reservoir is a capsule with a breakable seal arranged such that the seal may be broken under an applied pressure to allow the contents to enter through the instillation opening.

10. An apparatus comprising:
    a catheter for insertion into a hollow viscus of a subject, the catheter comprising:
    a drainage opening and an instillation opening at a distal end;
    an inlet port at a proximal end for instilling an instillation fluid;
    an outlet port at the proximal end for draining fluid from the viscus;
    a drainage channel connecting the drainage opening to the outlet port;
    an instillation channel connecting the inlet port to the instillation opening;
    a valve that is located proximate the drainage opening at the distal end for closing the drainage channel against the entry of fluid from the viscus;
    a valve control port at the proximal end for receiving a control fluid under pressure;
    and a control channel connecting the valve control port to the valve such that the valve is responsive to admitted control fluid under pressure to close the drainage channel, the catheter being such that flow of the control fluid to the valve is one way and the valve stays closed after the control fluid has entered the catheter under pressure;
    the apparatus further including a syringe or a plastic capsule, the syringe or the plastic capsule containing the control fluid and connected to the control channel to supply the control fluid under pressure.

11. A catheter according to claim 10, in which the valve comprises a balloon inflated by the control fluid to obstruct the drainage channel.

12. A catheter according to claim 10, comprising a reservoir of the control fluid connected to the valve control port for selective actuation by a user.

13. A catheter according to claim 10, comprising a balloon adjacent an external wall of the catheter near its distal end and connected through a balloon control channel to a balloon control port at the proximal end, the balloon being inflatable and deflatable to respectively increase and decrease the local diameter of the catheter to allow temporary anchoring of the catheter within the hollow viscus.

14. A catheter according to claim 10, in which the external wall of the catheter is coated with a hydrophilic layer.

15. A catheter according to claim 10, in which the ports at the proximal end are colour coded to distinguish them from one another.

16. A catheter according to claim 10, in which the ports at the proximal end are distinguishable from one another by having different shapes.

17. A catheter according to claim 10, comprising a reservoir of a fluid pharmaceutical preparation connected to the instillation opening.

18. The catheter according to claim 17, in which the fluid reservoir is a capsule with a breakable seal arranged such that the seal may be broken under an applied pressure to allow the contents to enter through the instillation opening.

* * * * *